United States Patent [19]

Nitzsche et al.

[11] Patent Number: 5,350,406
[45] Date of Patent: Sep. 27, 1994

[54] APPARATUS AND METHOD OF CONTROL FOR AN IMPLANTED ANTI-TACHYCARDIA DEVICE

[75] Inventors: Remi Nitzsche, Reynes; Marcel Limousin, Montrouge; Jean-Luc Bonnet; Christine Henry, both of Paris, all of France

[73] Assignee: ELA Medical, Montrouge, France

[21] Appl. No.: 995,034

[22] Filed: Dec. 22, 1992

[30] Foreign Application Priority Data

Dec. 31, 1991 [FR] France .................. 91 16364

[51] Int. Cl.$^5$ ............................... A61N 5/00
[52] U.S. Cl. ........................ 607/14; 128/705
[58] Field of Search ............ 607/5, 14, 15; 128/697, 128/700, 705

[56] References Cited

U.S. PATENT DOCUMENTS

| | | | |
|---|---|---|---|
| 3,946,725 | 3/1976 | Bolshov et al. | 128/2.06 R |
| 4,860,749 | 8/1989 | Lehmann | 128/419 PG |
| 5,042,497 | 8/1991 | Shapland | 607/14 |
| 5,054,485 | 10/1991 | Cohen | 607/14 |
| 5,205,283 | 4/1993 | Olson | 607/14 |

FOREIGN PATENT DOCUMENTS

| | | |
|---|---|---|
| 0360412 | 3/1990 | European Pat. Off. |
| 0395242 | 10/1990 | European Pat. Off. |
| 0401962 | 12/1990 | European Pat. Off. |
| 0436517 | 10/1991 | European Pat. Off. |

OTHER PUBLICATIONS

R. A. Dufault et al., Computers in Cardiology, "Dual Lead Fibrillation Detection For Implantable Defibrillators Via LMS Algorithm", Oct. 7, 1986, Boston US., pp. 163–166.

K. B. Otte et al., "Physiologische Elektrostimulation des Herzens Stand und Entwicklungsaussichten" Medizintechnik, Sep. 1984, pp. 84–91.

Von Kurt-Bernd Otte et al., "Physiologische Elektrostimulation des Herzens Stand Und Entwicklungsaussichten, 4550 Medizintechnik", 24 (1984) Sep., No. 3, Berlin, DD., p. 91.

Primary Examiner—Lee S. Cohen
Assistant Examiner—Marianne Parker
Attorney, Agent, or Firm—Davis Hoxie Faithfull & Hapgood

[57] ABSTRACT

Control of an anti-tachycardia device such as a defibrillator to apply a preselected programmed therapy in the event of ventricular tachycardia. The control includes comparison of the atrial and ventricular rhythms, and examination of the criteria of stability of the P-R intervals, of the stability of the R-R intervals, and of the acceleration of the ventricular rhythm subsequent to an atrioventricular desynchronization, thereby to ensure control of the antitachycardia device solely in the event of ventricular tachycardia.

6 Claims, 1 Drawing Sheet

APPARATUS AND METHOD OF CONTROL FOR AN IMPLANTED ANTI-TACHYCARDIA DEVICE

FIELD OF THE INVENTION

This invention relates to control of an implanted antitachycardia device, more particularly to controlling the programmed defibrillation therapy in response to fast ventricular rates.

BACKGROUND OF THE INVENTION

A defibrillator is a device that applies electric shocks to the heart in the event of ventricular fibrillation or ventricular tachycardia.

It is generally accepted that a heart rhythm exceeding, e.g., 300 beats per minute corresponds to a ventricular fibrillation, justifying triggering of the defibrillator. It also is generally accepted that a heart rhythm of less than, e.g., 150 beats per minute does not correspond to a ventricular tachycardia, but rather to a sinus rhythm or sinus tachycardia. Between these two values, the ventricle can have a ventricular tachycardia, a supraventricular tachycardia, or a bi-tachycardia, the latter being the superimposition of a ventricular tachycardia and a supraventricular tachycardia.

It is known to divide the spectrum of cardiac frequencies into bands to define different categories of tachycardia. European patent No. 360,412 refers to a well-tolerated tachycardia as between 150 and 175 beats per minute, an averagely tolerated tachycardia as between 175 and 200 beats per minute, and a poorly tolerated tachycardia as between 200 and 275 beats per minute. The document also refers to the ventricle frequency being greater than 275 beats per minute as undergoing fibrillation, and less than 150 beats per minute as a sinus rhythm.

Different therapies are programmed for each tachycardia category as a function of criteria, namely high frequency, sudden difference of frequency, and persistently high frequency. The different therapies include non-aggressive stimulations, aggressive stimulations, cardioversion shocks, and defibrillation shocks. They are applied in isolation or in succession as a function of the category of tachycardia defined according to the heart rate observed. The different therapies may be provided by an anti-tachycardia device in a known manner. It is noted that a defibrillator is one type of anti-tachycardia device which can deliver high energy shocks (up to several joules).

The approach of EP 360,412 to the problem of ventricular tachycardia is not fully satisfactory as it does not identify the type of tachycardia occurring in the ventricle: ventricular tachycardia, supraventricular tachycardia, or bi-tachycardia.

U.S. Pat. No. 4,860,749 describes a device that picks up the signals representative of the cardiac activity in both the ventricle and the atrium. By means of an algorithm using plural frequency thresholds and comparison to delays previously introduced for each patient, the device defines different types of tachycardia. According to this U.S. patent, the atrioventricular "AV" interval during a pathological tachycardia is greater than the AV interval in the case of tachycardia with an atrioventricular association of 1:1. During a preliminary electrophysiological examination, the doctor determines a threshold value and inserts it into the device. The algorithm tests the AV intervals with regard to this threshold value in order to define the type of tachycardia encountered.

U.S. Pat. No. 4,860,749 also refers to, in the case of the ventricular rate exceeding the atrial rate, automatically concluding the presence of a ventricular tachycardia. However, it is acknowledged that this event can correspond to other situations such as: sinus tachycardia with ventricular extra-systoles, 1:1 supraventricular tachycardia with loss of atrial detection, or atrial fibrillation with a fast ventricular rate and loss of atrial detection. Moreover, the criteria chosen in this U.S. patent, which presumes the presence of a ventricular tachycardia when the AV interval exceeds the value of the AV interval in sinus rhythm, can lead to misinterpretation insofar as it is acknowledged that supraventricular tachycardias induce unforeseeable variations of the AV interval.

SUMMARY OF THE INVENTION

It is an object of the present invention to remedy the foregoing disadvantages of the known prior art devices.

It is another object of the present invention to determine which of the ventricular tachycardia, supraventricular tachycardia, and bi-tachycardia is affecting the ventricle.

It is another object of the present invention is to provide apparatus and a method of control for an implanted antitachycardia device, according to the determination of the type of tachycardia affecting the ventricle. A further object of the present invention is to dispense with the electrophysiological examination of each particular patient, and to study the stability of various intervals before characterizing a tachycardia type, in order to avoid the delivery of defibrillation shocks that are not required.

Broadly, the present invention concerns methods and apparatus for controlling an implanted anti-tachycardia device as a function of the heart rhythm, wherein are defined (1) a slow heart rhythm below which there is no ventricular tachycardia, (2) a fast heart rhythm above which ventricular fibrillation or fast ventricular tachycardia may occur, and (3) an intermediary rhythm which is between the two fast rhythms and the one slow rhythm and for which a ventricular tachycardia is suspected. The invention is characterized in that, PR intervals and PR intervals are determined and evaluated over time, and, in the case of a determined intermediary rhythm, the programmed therapy is triggered by the anti-tachycardia device when all of the conditions of one of the following two groups of conditions are fulfilled:

(1) absence of 1:1 atrioventricular association, instability of the P-R intervals, and stability of the R-R interval; and (2) 1:1 atrioventricular association, and acceleration of the ventricular rhythm subsequent to an atrioventricular desynchronization.

In the preferred embodiment, the criteria of stability of the R-R intervals, of instability of the P--R intervals, and of acceleration of the ventricular rhythm are appraised over a selected number of cardiac cycles, e.g., from 2 to 32 cycles, more preferably, 8 cardiac cycles.

BRIEF DESCRIPTION OF THE DRAWING

Further features and advantages of the invention will be apparent upon consideration of the foregoing objects and the following detailed description of a preferred embodiment of the present invention, taken in conjunction with the accompanying drawing, in which.

DETAILED DESCRIPTION OF THE INVENTION

Figure 1:
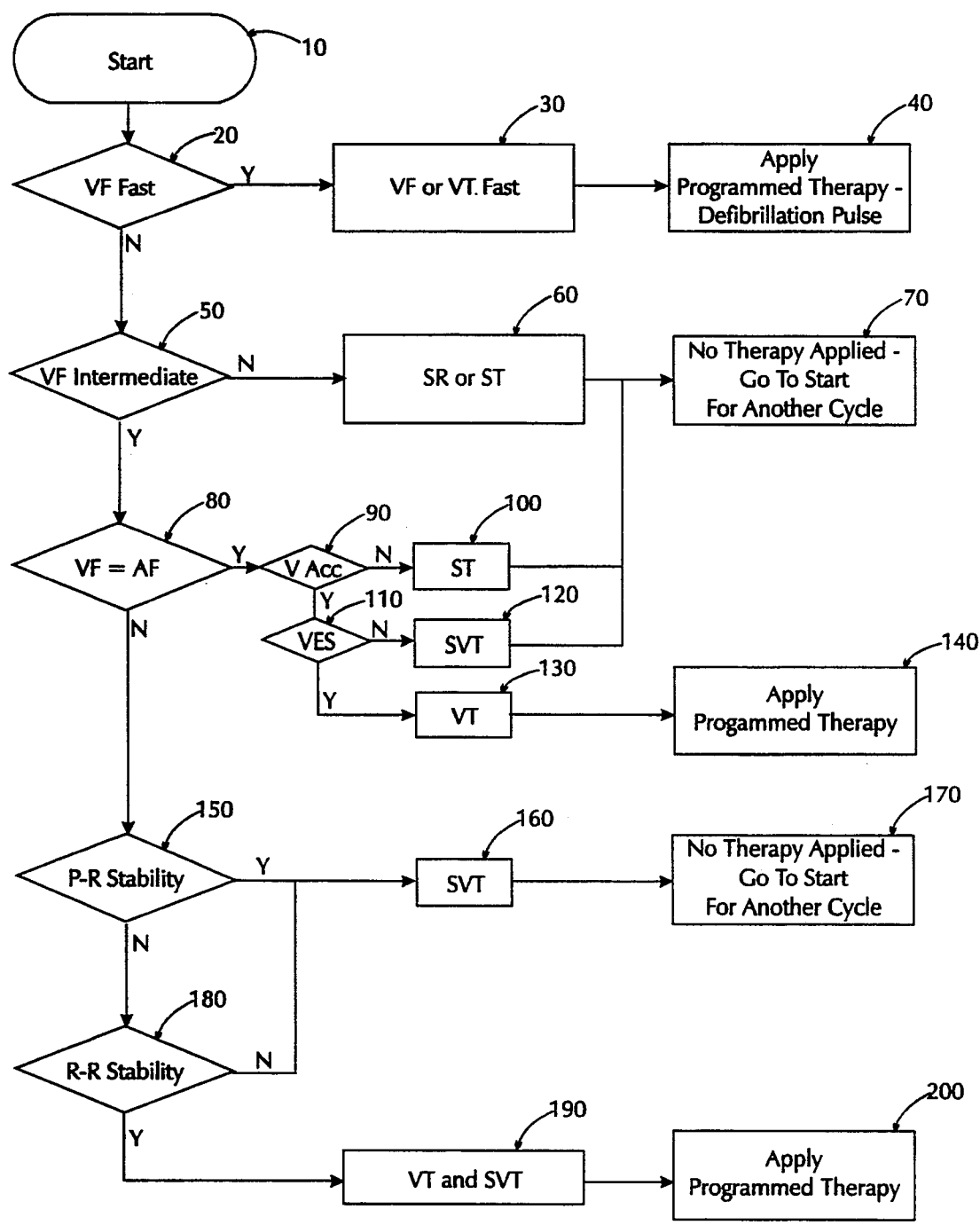
FIG. 1 is a flow chart diagraming a process for discriminating different types of tachycardia (middle column), and of the corresponding actions performed by a defibrillator (right-hand column) in response the determination in accordance with a preferred embodiment of the present invention.

In FIG. 1 the symbols below have the following associated meanings:

| Symbol | Meaning |
| --- | --- |
| VF | ventricular frequency, |
| AF | atrial frequency, |
| SR | sinus rhythm, |
| ST | sinus tachycardia, |
| SVT | supraventricular tachycardia, |
| VT | ventricular tachycardia, |
| P-R Stability | stability of the P-R intervals (between a P wave and the following R wave) over a predetermined number of previous cycles, |
| R-R Stability | stability of the R-R intervals (between two successive R waves) over a predetermined number of previous cycles, |
| VF | ventricular fibrillation. |
| Fast VF | the ventricular frequency is in excess of a programmed frequency, characteristic of either ventricular fibrillation VF or fast ventricular tachycardias (e.g., 300 beats per minute), |
| VF Intermediate | the ventricular frequency is intermediary, i.e., below the programmed frequency characteristic of ventricular fibrillation, (e.g., 300 beats per minute) and above the frequency of suspected ventricular tachycardia (e.g., 150 beats per minute), |
| AF = VF | 1:1 association of atrioventricular rhythms, |
| V Acc | the ventricular rhythm has accelerated and remained accelerated during a predetermined number of cycles, typically 8, |
| VES | the acceleration of the ventricular rhythm was triggered at the time of an atrioventricular desynchronization defined as ventricular extra-systole. |

An atrioventricular desynchronization corresponds to the appearance of a P-R interval that is either abnormally long, e.g., in excess of 300 ms, or abnormally short, e.g., below 31 ms.

With reference to the flow chart in FIG. 1, the routine begins at start step 10. The analysis conducted in the process illustrated in FIG. 1 is performed at each ventricular detection, i.e., once per cardiac cycle. The ventricular interval is first evaluated at step 20 to determine if it corresponds to the fast ventricular frequency Fast VF. If it is, then at step 30 it is concluded that the heart is incurring either ventricular fibrillation Fast VF or fast ventricular tachycardia Fast VT. The action performed by the anti-tachycardia device in response to either condition at step 40 is the application of a suitable defibrillation pulse in the normal manner.

If the ventricular frequency VF is not fast at step 20, then it is evaluated at step 50 to determine if it is intermediary. If the ventricular frequency VF is neither fast nor intermediary, then it is concluded at step 60 that the heart is in either the sinus rhythm SR or sinus tachycardia ST state, and, at step 70, no therapy is applied and a further cardiac cycle must be awaited.

If the ventricular frequency VF is intermediary, then at step 80 the ventricular frequency is checked to determine if there is a 1:1 association with the atrioventricular rhythms (AF=VF).

If there is a 1:1 association, the ventricular rhythm is examined at step 90 for acceleration. If no acceleration of the ventricular rhythm has occurred, then it is concluded at step 100 that the heart is experiencing sinus tachycardia, no therapy is applied, and a further cardiac cycle should be awaited (step 70).

If, however, there has been acceleration of the ventricular rhythm at step 90, then the atrioventricular desynchronization VES is checked at step 110. If there is no atrioventricular desynchronization VES, then it is concluded at step 120 the heart is incurring supraventricular tachycardia SVT, no therapy is applied, and a further cardiac cycle should be awaited (step 70).

If, however, there has been acceleration of the ventricular rhythm (step 90) and atrioventricular desynchronization VES (step 110), then it is concluded at step 130 that the heart is incurring ventricular tachycardia VT and in response thereto the anti-tachycardia device applies the appropriate programmed therapy at step 140.

In the case of a determined intermediary ventricular frequency VF (step 50) in the absence of 1:1 atrioventricular association (step 80), the P-R intervals are then evaluated for stability at step 150. If the P-R intervals are stable, then it is concluded at step 160 that the heart is incurring supraventricular tachycardia SVT, no therapy is applied, and a further cardiac cycle should be awaited (step 170).

If, however, the P-R intervals are not stable, then the R-R intervals are evaluated at step 180 to determine their stability. If the R-R intervals are not stable, then it is concluded at step 160 that the heart is incurring supraventricular tachycardia SVT and a further cardiac cycle should be awaited (step 170).

If, however, the P-R intervals are not stable and the R-R intervals are stable, then it is concluded at step 190 that the heart is incurring supraventricular tachycardia SVT and ventricular tachycardia VT, i.e., bi-tachycardia, and the antitachycardia device applies the appropriate programmed therapy at step 200.

In the event of a determined intermediary rhythm, the programmed therapy applied at steps 140 and 200 is either the application of an automatic anti-ventricular tachycardia sequence, or the application of cardioversion shocks, or the application of a combination of the foregoing actions, e.g., graduated from a low energy to a high energy. Such therapy is conventional.

As is apparent from the foregoing, control of an implanted anti-tachycardia device in accordance with the invention requires sensing cardiac activity in the atrial chamber and in the ventricular chamber. Accordingly, two conventional endocardial leads (and the conventional anti-tachycardia and/or defibrillation electrodes) are provided for this purpose. The detection of atrial and ventricular complexes and the measuring of the amplitude of, and interval between the occurrence of these complexes are performed by conventional electronic means, e.g., digital microprocessor controlled devices having sense amplifiers, analog signal conditioning circuits, analog-to-digital conversion circuits and suitable memory, buffers and registers for time-based digital data processing and manipulation. The present invention is preferably implemented in software, and is preferably applied following acquisition of the atrial and ventricular cardiac electric signals by conventional atrial and ventricle sense amplifiers and more preferably after the acquired signals have been suitably conditioned and converted to digital form in a usual manner. Representative electronic circuits for acquiring the cardiac signals and PR and RR intervals are those found in the series of dual chamber pacemakers available from Ela Medical, Montrouge, France, offered under the CHORUS trademark. The method and apparatus also could be implemented using discrete circuitry or finite element state machines, if desired. The result of the determination to apply the programmed therapy is to deliver suitable control signals by the microprocessor to the anti-tachycardia cardioversion or defibrillator stimulation pulse generating circuit so that such device can deliver the appropriate pulse or pulse sequence.

One skilled in the art will appreciate that the present invention can be practiced by other than the described embodiments, which are presented for purposes of illustration and not of limitation.

We claim:

1. A method of controlling an implanted anti-tachycardia device as a function of a patient's heart rhythm, comprising the steps of:

defining a slow heart rhythm below which there is no ventricular tachycardia, defining a fast heart rhythm above which ventricular fibrillation or fast ventricular tachycardia occur, and defining an intermediary rhythm between said fast and slow rhythms and for which a ventricular tachycardia is suspected;

detecting atrial P wave events and ventricular R wave events;

analyzing the detected P wave and R wave events and determining therefrom a sensed heart rhythm, an acceleration of the ventricular rhythm, an atrioventricular association ratio, an R-R interval between successive R waves, a stability of R-R intervals, a P-R interval between a P wave and the following R wave, an instability of P-R intervals, and a ventricular rhythm;

identifying a heart rhythm corresponding to said intermediary heart rhythm; and in response thereto triggering said antitachycardia device to provide a preselected programmed therapy in response to one of a first condition or a second condition wherein the first condition includes a determined absence of 1:1 atrioventricular association, instability of the P-R intervals, and stability of the R-R interval; and wherein the second condition includes a determined 1:1 atrioventricular association and acceleration of the ventricular rhythm subsequent to an atrioventricular desynchronization.

2. The method of claim 1 wherein determining each of the stability of said R-R intervals, instability of said P-R intervals, and acceleration of the ventricular rhythm parameters further comprises determining the stability of said R-R intervals, instability of said P-R intervals, and acceleration of the ventricular rhythm based on P wave and R wave events monitored over a selected number of cardiac cycles.

3. The method of claim 2 wherein determining the stability of said R-R intervals, instability of said P-R intervals, and acceleration of the ventricular rhythm further comprises determining said parameters based on monitored P wave and R wave events occurring during a period that is 8 cardiac cycles.

4. In an implanted anti-tachycardia device, apparatus for applying a programmed anti-tachycardia therapy to cardiac tissue including circuits for receiving cardiac signals corresponding to atrial P wave and ventricular R wave heart activity comprising:

means for sensing a heart rhythm, means for determining whether the heart rhythm is one of a slow heart rhythm below which there is no ventricular tachycardia, a fast heart rhythm above which ventricular fibrillation or fast ventricular tachycardia may occur, and an intermediary rhythm between said fast and slow rhythms;

means for analyzing said atrial P waves and ventricular R waves and determining therefrom a P-R interval, a P-R interval instability, an R-R interval, an R-R interval stability, an atrioventricular association ratio, a ventricular rhythm, and an acceleration of the ventricular rhythm; and means for triggering the anti-tachycardia device to apply a preselected programmed therapy in response to the determining means determining that there is an intermediary rhythm and in response to the analyzing and determining means determining that there is one of a first condition and a second condition, wherein the first condition includes a determined absence of 1:1 atrioventricular association, instability of the P-R intervals, and stability of the R-R interval; and wherein the second condition includes a determined 1:1 atrioventricular association, and acceleration of the ventricular rhythm subsequent to an atrioventricular desynchronization.

5. The apparatus of claim 4 wherein said analyzing and determining means determines the stability of said R-R intervals, the instability of said P-R intervals, and the acceleration of the ventricular rhythm based on P wave and R wave heart activity monitored over a preselected number of cardiac cycles.

6. The apparatus of claim 4 wherein said analyzing and determining means determines the stability of said R-R intervals, the ability of said P-R intervals, and the acceleration of the ventricular rhythm based on P wave and R wave heart activity monitored over 8 cardiac cycles.

* * * * *

UNITED STATES PATENT AND TRADEMARK OFFICE
CERTIFICATE OF CORRECTION

PATENT NO. : 5,350,406
DATED : September 27, 1994
INVENTOR(S) : Nitzsche et al.

It is certified that error appears in the above—identified patent and that said Letters Patent is hereby corrected as shown below:

Column 2, line 46, "PR" should be --RR--;
                                [Spec. p. 4, line 21]

Column 2, line 59, "P--R" should be --P-R--;
                                [Spec. p. 5, line 10]

Column 5, line 56, after "rhythm" delete "parameters"
                                [Examiner's Amendment, dated 3/29/94];

Column 6, line 52, "ability" should be --instability--;
                                [Amendment 3/17/94, p. 4, line 19]

Signed and Sealed this

Twenty-eight Day of March, 1995

Attest:

BRUCE LEHMAN

*Attesting Officer*      *Commissioner of Patents and Trademarks*